US010004566B2

(12) United States Patent
Park et al.

(10) Patent No.: US 10,004,566 B2
(45) Date of Patent: Jun. 26, 2018

(54) ELECTROMAGNETIC ACTUATING DEVICE INCLUDING POSITION-ADJUSTABLE COIL

(71) Applicant: INDUSTRY FOUNDATION OF CHONNAM NATIONAL UNIVERSITY, Gwangju (KR)

(72) Inventors: Suk Ho Park, Gwangju (KR); Jong Oh Park, Goyang-si (KR); Seong Young Ko, Gwangju (KR); Hyun Chul Choi, Gwangju (KR); Semi Jeong, Jeonju-si (KR); Cheong Lee, Gwangju (KR); Gwang Jun Go, Gwangju (KR)

(73) Assignee: Industry Foundation of Chonnam National university, Gwangju (KR)

( * ) Notice: Subject to any disclaimer, the term of this patent is extended or adjusted under 35 U.S.C. 154(b) by 248 days.

(21) Appl. No.: 15/064,951

(22) Filed: Mar. 9, 2016

(65) Prior Publication Data

US 2016/0262841 A1    Sep. 15, 2016

(30) Foreign Application Priority Data

Mar. 12, 2015  (KR) .................. 10-2015-0034475

(51) Int. Cl.
*A61B 19/00* (2006.01)
*A61B 34/00* (2016.01)
*A61B 34/20* (2016.01)
*A61B 5/06* (2006.01)

(52) U.S. Cl.
CPC ............. *A61B 34/73* (2016.02); *A61B 5/06* (2013.01); *A61B 34/20* (2016.02); *A61B 2034/732* (2016.02)

(58) Field of Classification Search
CPC .................................. A61B 5/06; A61B 34/20
USPC .................................. 128/899; 600/424, 427
See application file for complete search history.

(56) References Cited

U.S. PATENT DOCUMENTS

| 6,311,082 | B1 | 10/2001 | Creighton et al. |
| 2002/0143252 | A1 | 10/2002 | Dunne et al. |
| 2007/0016006 | A1 | 1/2007 | Shachar |
| 2012/0281330 | A1 | 11/2012 | Abbott et al. |

FOREIGN PATENT DOCUMENTS

| KR | 10-1001291 B1 | 12/2010 |
| KR | 10-1128045 B1 | 3/2012 |
| KR | 10-1272156 B1 | 6/2013 |

OTHER PUBLICATIONS

Korean Office Action dated Apr. 18, 2016.

*Primary Examiner* — John Lacyk
(74) *Attorney, Agent, or Firm* — Rabin & Berdo, P.C.

(57) ABSTRACT

An electromagnetic actuating device. A coil unit generates magnetic field toward a medical device inserted into a human body. An actuator drives the coil unit to move back and forth, thereby adjusting the rate of a change in magnetic force or magnetic field applied to the medical device. The coil unit moves linearly back and forth depending on the body shape of a subject and the body part to be diagnosed, such that actuation force is efficiently supplied to the medical device.

3 Claims, 4 Drawing Sheets

ELECTROMAGNETIC ACTUATING DEVICE INCLUDING POSITION-ADJUSTABLE COIL

CROSS REFERENCE TO RELATED APPLICATION

The present application claims priority to Korean Patent Application No. 10-2015-0034475, filed Mar. 12, 2015, the entire contents of which is incorporated herein for all purposes by this reference.

BACKGROUND OF THE INVENTION

Field of the Invention

The present invention generally relates to an electromagnetic actuating device for actuating a medical device inserted into a human body. More particularly, the present invention relates to an electromagnetic actuating device able to efficiently supply actuation force to a medical device depending on the body shape of a subject, the body part to be diagnosed, and the actuating mechanism of the medical device.

Description of the Related Art

In general, medical devices are operated using wireless or wired actuations to diagnose or cure lesions present in internal organs, such as blood vessels and digestive organs. Among such medical devices, a miniature medical device inserted into a human body to be used for diagnosis may be difficult to control since it may not be suitable to be equipped with an on-board battery or an actuator.

Recently, studies of using magnetic fields to control miniature medical devices inserted into human bodies have been conducted. Medical devices are partially or entirely a magnetic material without a battery or a separate actuator such that they can be controlled using magnetic fields. When a battery or an actuator is replaced with a magnetic material, medical devices can be designed to have a very small size. Medical devices minimized in sizes allow for minimally invasive surgery. This minimizes the size of an incision during surgery, thereby advantageously reducing the pain and recovery periods of patients.

Medical devices having magnetic bodies can be controlled using a magnetic field generating apparatus disposed externally. The magnetic field generating apparatus is divided into a permanent magnet and an electromagnet. The permanent magnet can actuate a medical device by controlling the distance and the direction of magnetic field between the medical device and the permanent magnet. In this case, however, the movement and the rate of the medical device are limited, which are problematic.

Medical devices actuated using electromagnets can be controlled by applying currents to coils disposed externally in a fixed position. Here, it is possible to realize the intended actuation of medical devices by controlling, for example, the intensities and directions of currents applied to the coils. The use of electromagnets facilitates control compared to the use of permanent magnets. In addition, electromagnets can rapidly control the movement of medical devices depending on the characteristics of coils.

However, as a medical device becomes more distant away from an electromagnetic actuating device, the magnitude of magnetic field applying to the medical device is rapidly reduced. In this case, in order to control the medical device, a large amount of current must be applied to coils depending on the distance, which is problematic. More specifically, in a related-art electromagnetic actuating device for generating magnetic field toward a table on which a subject is lying, a coil is fixedly disposed. Thus, when the subject is diagnosed, the distance between the coil and the medical device changes depending on the body shape of the subject and the body part to be diagnosed. It is inefficient, in terms of control precision and power consumption, to control the amount of current applied to the coil considering the intensity of magnetic field changing depending on the distance.

In addition, in order to increase magnetic force, the electromagnet may be configured as a combination of a coil and a magnetic core. As described above, in order to increase magnetic force, a larger magnitude of magnetic force can be provided as the electromagnet (including the coil and the magnetic core) approaches the subject. Although the use of the magnetic core increases magnetic force, the magnetic core also increases the inductance of the electromagnet, whereby response to a change in magnetic field is delayed, which is problematic. When the medical device is actuated based on rotation, a rotating magnetic field is used. When a rapidly-changing magnetic field, such as a rotating magnetic field, is required, the magnetic core obstructs the actuation of the medical device, which is problematic.

In this case, it is advantageous for rotational actuation to place the coil part of the electromagnet to be close to the subject and set the position of the magnetic core behind the subject. Consequently, a structure allowing the relative positions of the coil and the magnetic core of the electromagnet to be adjusted and the overall position of the electromagnet (including the core and the magnetic core) to be changeable is advantageous for the actuation of the medical device. That is, an electromagnetic actuating device able to efficiently supply actuation force to a medical device depending on the body shape of a subject and the body part to be diagnosed, and the actuating mechanism of the medical device is required.

The information disclosed in the Background of the Invention section is only for the enhancement of understanding of the background of the invention, and should not be taken as an acknowledgment or as any form of suggestion that this information forms a prior art that would already be known to a person skilled in the art.

RELATED ART DOCUMENTS

Patent Documents

Patent Document 1: US Patent Application Publication No. 2012-0281330
Patent Document 2: U.S. Pat. No. 6,311,082

SUMMARY OF THE INVENTION

Accordingly, the present invention has been made keeping in mind the above problems occurring in the related art, and the present invention is intended to propose an electromagnetic actuating device able to efficiently supply actuation force to a medical device depending on the body shape of a subject, the body part to be diagnosed, and the actuating mechanism of the medical device.

In order to achieve the above object, according to one aspect of the present invention, an electromagnetic actuating device may include: a coil unit generating magnetic field toward a medical device inserted into a human body; and an actuator driving the coil unit to move back and forth, thereby adjusting rate of a change in magnetic force or magnetic field applied to the medical device.

The coil unit may include: a solenoid coil generating magnetic field in an axial direction; and a magnetic core focusing magnetic flux in the solenoid coil. The actuator may drive the magnetic core or the solenoid coil to move back and forth.

The actuator may include: an actuating screw; and a first motor supplying power to the actuating screw. The magnetic core moves through pitch shifting in line with rotation of the driving screw.

The coil unit may further include a core housing inside of which the magnetic core is disposed, the core housing having a fastening hole formed in the inner portion thereof, through which the actuating screw is screwed. The core housing may move through pitch shifting in line with rotation of the actuating screw.

The core housing may include one or more splines on an outer circumferential surface thereof, the splines guiding the core housing in a straight direction when the actuating screw rotates.

The actuator may include one or more splines on an outer circumferential surface thereof: a pinion gear; a second motor supplying power to the pinion gear. The solenoid coil moves back and forth in line with rotation of the pinion gear.

The coil unit may further include a coil housing with the solenoid coil wound on an outer circumferential surface thereof, the coil housing including a rack engaged with the pinion gear. The coil housing may move back and forth in line with rotation of the pinion gear.

According to the present invention, it is possible to efficiently supply actuation force to the medical device by driving the coil unit to move back and forth depending on the body shape of a subject and the body part to be diagnosed.

In addition, according to the present invention, the coil unit can be changed in position to minimize the distance to the medical device therefrom, whereby the electromagnetic actuating device has superior power efficiency.

Furthermore, according to the present invention, the actuator can adjust the relative positions of the solenoid coil and the magnetic core, thereby efficiently changing magnetic flux generated in the solenoid coil.

BRIEF DESCRIPTION OF THE DRAWINGS

The above and other objects, features and advantages of the present invention will be more clearly understood from the following detailed description when taken in conjunction with the accompanying drawings, in which:

FIGS. 1A and 1B illustrate the external appearance of an electromagnetic actuating device according to an exemplary embodiment of the present invention and the shape of a subject into which a medical device is inserted, in which FIG. 1A illustrates a case in which a relatively-small body part such as the head is to be treated, and coil units are varied in length to approach the head to be closer thereto, and FIG. 1B illustrates a case in which the lengths of the coil units are varied to diagnose and treat a condition existing in the chest of the subject;

FIGS. 5A to 5C illustrate the configurations in which the relative positions of the solenoid coil and the magnetic core according to the present embodiment are adjusted, in which FIG. 5A illustrates the overall configuration of the actuator and the coil unit coupled to each other, FIG. 5B illustrates the configuration in which the solenoid coil has moved forwards and the magnetic core has moved backwards, and FIG. 5C illustrates the configuration in which the solenoid coil has moved backwards and the magnetic core has moved forwards.

DETAILED DESCRIPTION OF THE INVENTION

Figure 1A:
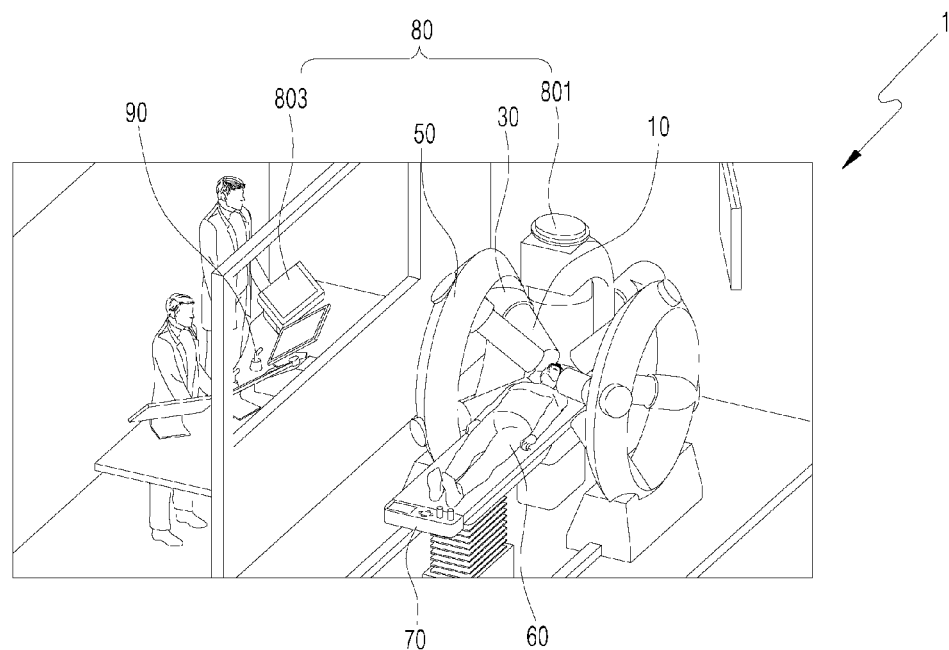

Reference will now be made in greater detail to exemplary embodiments of the present invention, examples of which are illustrated in the accompanying drawings. It should be understood, however, that the present invention is by no means limited or restricted thereto. Wherever possible, the same reference numerals will be used throughout the drawings and the description to refer to the same or like parts.

The objects and effects of the present invention will be more clearly understood from the following description but are by no means limited to the following description.

The above and other objects, characteristics, and advantages of the present invention will be more clearly understood from the following detailed description. In the following description of the present invention, detailed descriptions of known functions and components incorporated herein will be omitted in the case that the subject matter of the present invention may be rendered unclear thereby.

Figure 1B:
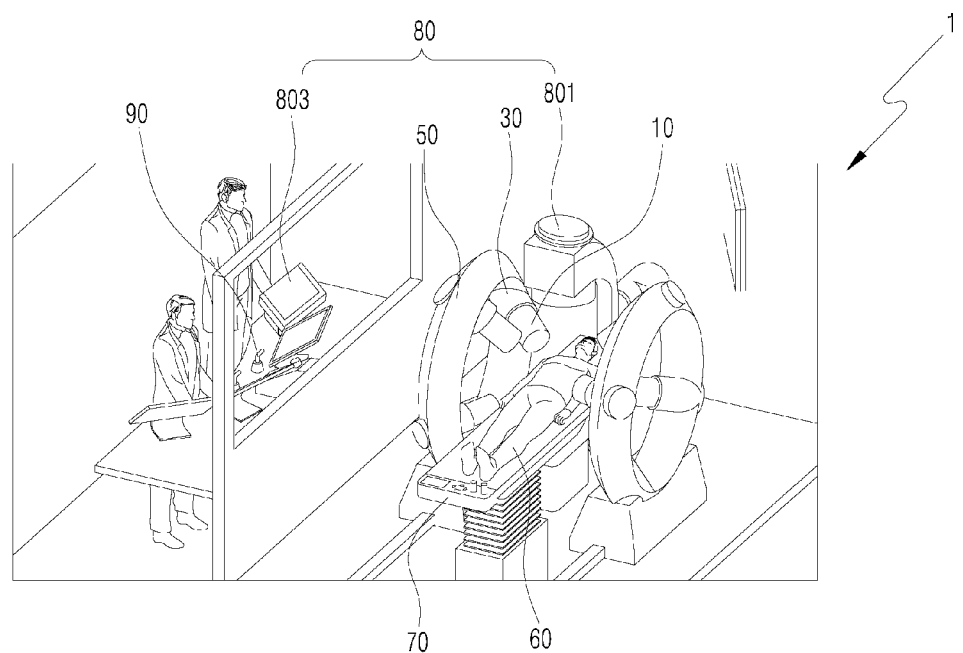

FIGS. 1A and 1B illustrate the external appearance of an electromagnetic actuating device 1 according to an exemplary embodiment of the present invention and the shape of a subject 60 into which a medical device is inserted. FIG. 1A illustrates a case in which a relatively-small body part such as the head is to be treated, and coil units 10 are varied in length to approach the head to be closer thereto, and FIG. 1B illustrates a case in which the lengths of the coil units 10 are varied to diagnose and treat a condition existing in the chest of the subject 60.

Referring to FIGS. 1A and 1B, the electromagnetic actuating device 1 according to the present embodiment includes frames 50, the coil units 10, actuators 30, a positioning unit 80, and a control 90. The electromagnetic actuating device 1 can actuate and control the medical device inserted into the human body of the subject 60. The medical device according to the present embodiment may be implemented as a device, such as a microrobot, a microcapsule, or a capsule-shaped endoscope, which can be inserted into human bodies to cure cardiovascular diseases or to release drugs therein.

Medical devices inserted into human bodies have a wide range of diagnosis applications, and thus are more advantageous than typical catheter treatments. However, it is difficult to integrate an actuator, a sensor, a wireless communications module, a medical delivery function, a battery, and the like to a microscale medical device. In order to overcome this restriction, active studies have recently been conducted with the intention of actuating and controlling microscale medical devices using electromagnetic fields.

A medical device has one or more magnetic bodies therein, with which the medical device can perform specific motions, such as aligning, rotation, and propulsion with respect to the advancing direction, in response to a rotating magnetic field or a gradient magnetic field applied externally. For example, an electromagnet may be used to generate magnetic field externally of the medical device. According to the present embodiment, the medical device may be aligned with an intended advancing direction or may be provided with rotational force in the intended advancing direction from a rotational magnetic field of magnetic field generated by the electromagnetic actuating device 1. In addition, the medical device may be externally provided with propulsion from a gradient magnetic field of the magnetic field generated by the electromagnetic actuating device 1.

The detailed configuration of the medical device actuated by an electromagnetic field will not be described since various examples thereof are specifically described in Korean Patent No. 10-1128045, titled "DRILLING MICROROBOT SYSTEM USING ELECROMAGNETIC FIELD", Korean Patent No. 10-1001291, titled "3D ELECTROMAGNETICALLY ACTUATED MICROROBOT ACTUATING MODULE AND SYSTEM", Korean Patent No. 10-1272156, titled "BLOOD VESSEL CURING MICROROBOT SYSTEM AND CONTROL METHOD THEREOF", etc.

The electromagnetic actuating device 1 includes a pair of frames 50. The coil units 10 and the actuators 30 are disposed on the frames 50. The frames 50 may be disposed on both sides of a table 70, such that the coil units 10 can generate magnetic fields toward the subject 60. Eight actuators 30 and four coil units 10 may be disposed at equal distances on each of the frames 50. In this case, the coil units 10 may be disposed on the frames 50 such that the lengths thereof can be varied in the direction toward the medical device inserted into the subject 60.

The positioning unit 80 can detect the position and orientation of the medical device inserted into the subject 60. The positioning unit 80 includes an X-ray module 801 emitting X-rays toward the subject 60 and a display module 803 displaying the position of the medical device based on image information obtained using the X-ray module 801. Although not illustrated in the drawings, the X-ray module 801 may include an X-ray source and an X-ray detector. The display module 803 may perform image processing using X-rays detected by the X-ray detector.

The positioning unit 80 can monitor, for example, the current status of the subject 60 and the real-time position and orientation of the medical device by obtaining real-time X-ray images from the X-ray module 801 and the display module 803. According to the present embodiment, image data acquired prior to treatment including accurate positions of a lesion or blood vessels around the lesion obtained using computed tomography (CT) or magnetic resonance imaging (MRI) may be stored in the display module 803.

The control 90 controls the actuators 30 to drive the coil units 10 to linearly move back and forth depending on the position of the medical device obtained from the positioning unit 80. In addition, the control 90 controls the intensities of currents and the directions of magnetic fields applied to the coil units 10.

Figure 2:
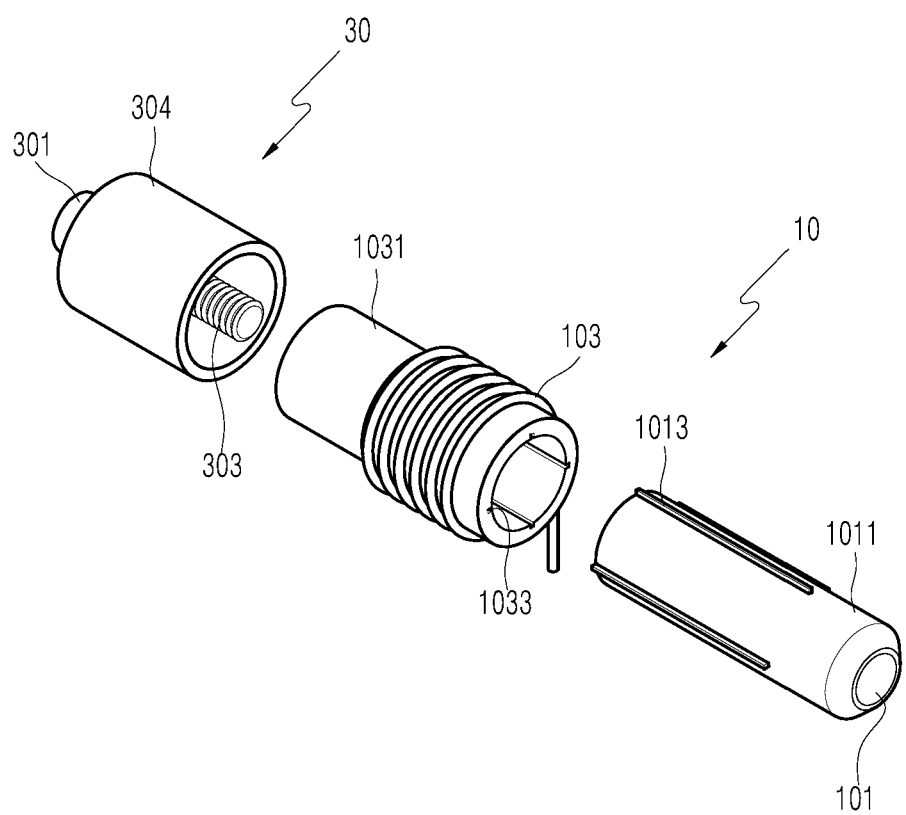
FIG. 2 is a perspective view illustrating an actuator and a coil unit according to an exemplary embodiment of the present invention, the coil unit being engaged with the actuator such that the coil unit can reciprocate.

FIG. 2 is a perspective view illustrating an actuator 30 and a coil unit 10 according to an exemplary embodiment of the present invention, the coil unit 10 being engaged with the actuator 30 such that the coil unit 10 can reciprocate. The coil unit 10 can generate magnetic field toward a medical device. A coil wound on a metal or polymer core or a magnetic core may be provided within the coil unit 10. The actuator 30 can actuate the coil unit 10 to move back and forth with respect to the direction of the medical device.

Referring to FIG. 2, the coil unit 10 includes a solenoid coil 103 generating magnetic field in the axial direction and a magnetic core 101 focusing magnetic flux in the solenoid coil 103. The magnetic core 101 may be formed of a ferromagnetic material having low energy loss and high permeability. Since the magnetic core 101 is formed of wrought iron having high permeability, the magnetic core 101 can generate a strong magnetic field from a small amount of current.

The actuator 30 can adjust the rate of change of magnetic force and magnetic field applied to the medical device by driving the coil unit 10 back and forth. More particularly, the actuator 30 can simultaneously actuate the magnetic core 101 and the solenoid coil 103 to reciprocate linearly. In this case, both the magnetic core 101 and the solenoid coil 103 move close to the subject, whereby a greater amount of magnetic force is applied to the medical device.

In addition, the actuator 30 can adjust the relative positions of the magnetic core 101 and the solenoid coil 103 by linearly moving the magnetic core 101 or the solenoid coil 103 back and forth. In this case, the relative positions may be adjusted such that the solenoid coil 103 moves toward the subject and the magnetic core 101 moves away from the subject. This adjustment of the relative positions may minimize the inductance of an electromagnet under the influence of the magnetic core 101, thereby accelerating a change in the magnetic field applied to the medical device.

It is preferable that the actuator 30 is implemented as an actuating device free from the influence of a magnetic body. For example, the actuator 30 includes an actuating screw 303 and a first motor 301 supplying power to the actuating screw 303.

The coil unit 10 further includes a core housing 1011 inside of which the magnetic core 101 is disposed. The core housing 1011 has a fastening hole 1015 formed in the inner portion thereof, through which the actuating screw 303 can be screwed. The core housing 1011 can move through pitch shifting in line with the rotation of the actuating screw 303.

The core housing 1011 has one or more splines 1013 on the outer circumference thereof. When the actuating screw 303 rotates, the splines 1013 guide the core housing 1011 in the straight direction.

The coil unit 10 further includes a coil housing 1031 on the outer circumference of which the solenoid coil 103 is wound. The coil housing 1031 has spline grooves 1033 on the inner surface thereof. The spline grooves 1033 engage with the splines 1013 such that the core housing 1011 can slide along the inner surface of the coil housing 1031. The coil housing 1031 is movable back and forth in line with the rotation of a pinion gear 305 (FIG. 3), which will be described later.

Figure 3:
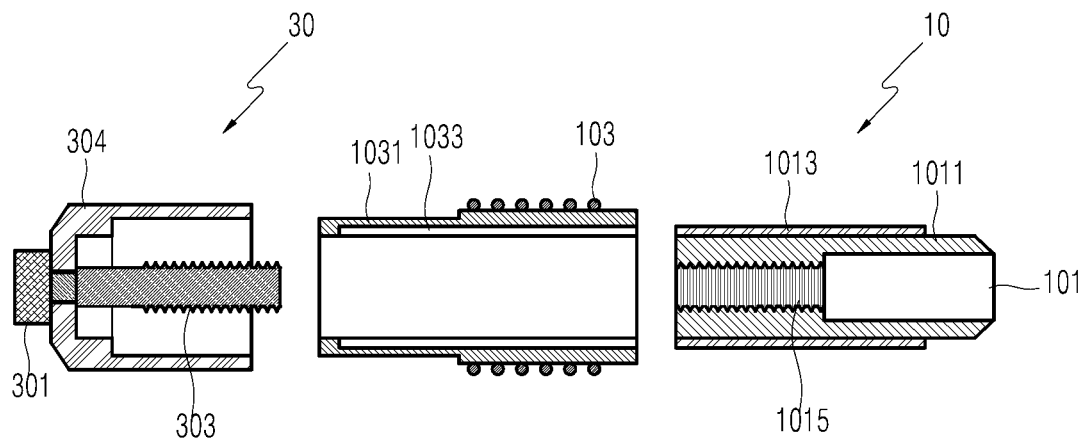
FIG. 3 is an exploded cross-sectional view illustrating the coil unit 10 the actuator according to the present embodiment.

FIG. 3 is an exploded cross-sectional view illustrating the coil unit 10 and the actuator 30 according to the present embodiment. Referring to FIG. 3, the actuator 30 includes the actuating screw 303, the first motor 301, and a screw housing 304 to actuate the magnetic core 101 to move back and forth. The screw housing 304 has a space therein, in which the core housing 1011 and the coil housing 1031 move back and forth and are engaged with each other.

The actuating screw 303 is disposed within the screw housing 304, and one end of the actuating screw 303 is connected to the first motor 301. Male threads are formed on the outer circumference of the actuating screw 303, such that the other end of the actuating screw 303 can rotate to be screwed into the fastening hole 1015 of the core housing 1011 having female threads.

The coil housing 1031 has the shape of a cylinder having an inner hole extending therethrough, and can be engaged with the screw housing 304 such that the coil housing 1031 is movable back and forth within the screw housing 304. The coil housing 1031 has spline grooves 1033 in the inner surface abutting the core housing 1011, the spline grooves 1033 corresponding to the splines 1013 of the core housing 1011.

When the core housing 1011 engaged with the actuating screw 303 rotates, the splines 1013 slide along the spline grooves 1033. The splines 1013, which guide the rotation of the actuating screw 303 in the straight direction, allow the core housing 1011 to move through gear pitch shifting.

Figure 4:
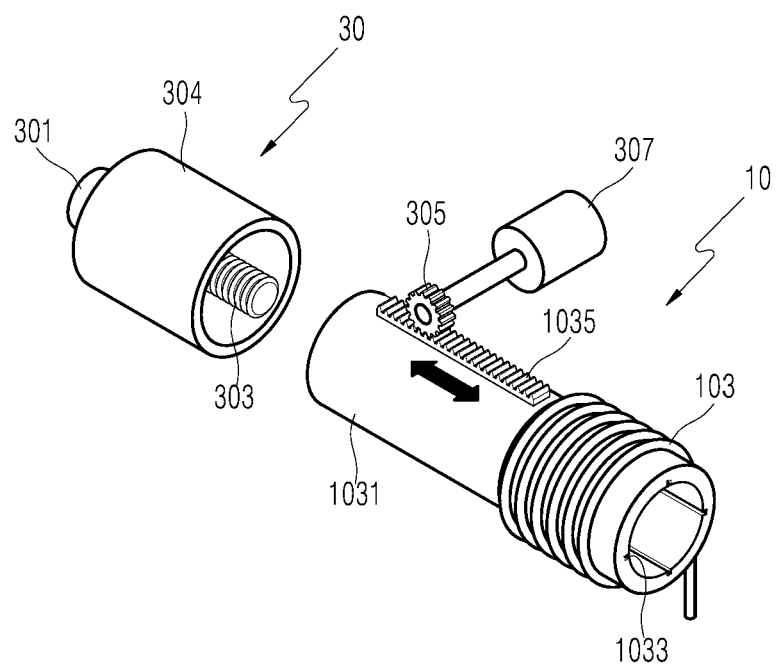
FIG. 4 is a perspective view illustrating the actuator and the coil housing engaged with the actuator such that the coil housing is movable back and forth.

FIG. 4 is a perspective view illustrating the actuator and the coil housing engaged with the actuator such that the coil housing is movable back and forth. Referring to FIG. 4, the actuator 30 further includes the pinion gear 305 and a second motor 307 in order to move the solenoid coil 103 back and forth. The second motor 307 supplies power to the pinion gear 305.

The solenoid coil 103 is wound on the circumferential surface of the upper part of the coil housing 1031, and a rack is fixed to the lower part of the coil housing 1031 to engage with the pinion gear 303. The coil housing 1031 is movable back and forth in line with the rotation of the pinion gear 305.

Alternatively, the actuator 30 for changing the position of the coil unit 10 may be implemented as a driving means, such as a hydraulic or linear motor, an encoder, or the like.

According to the present embodiment as described above, the position of the coil unit 10 may be changed by the actuator 30. In particular, the actuator 30 may adjust the relative positions of the magnetic core 101 and the solenoid coil 103 by actuating the magnetic core 101 or the solenoid coil 103 forwards or backwards.

Figure 5A:
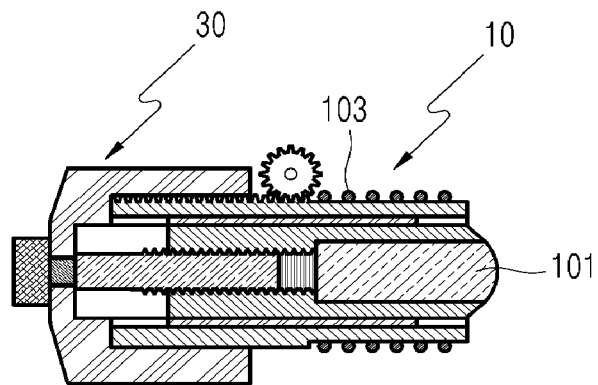
Figure 5B:
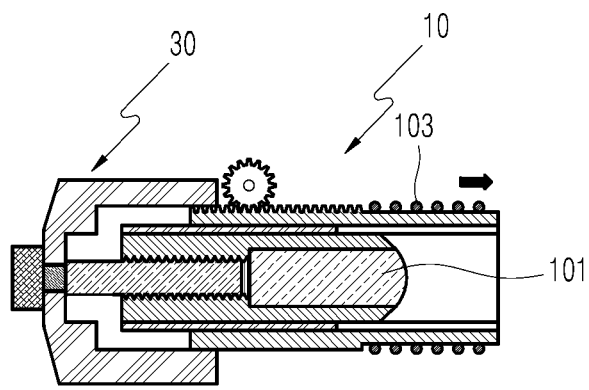
Figure 5C:
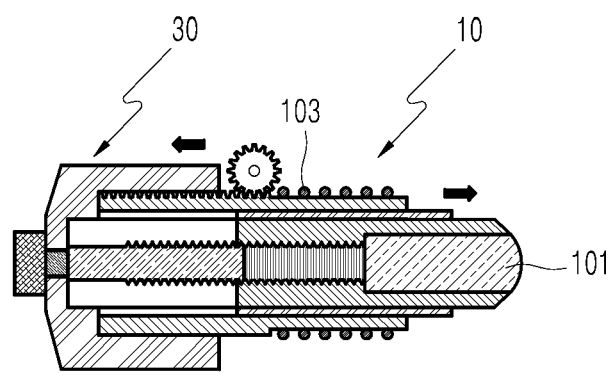

FIGS. 5A to 5C illustrate the configurations in which the relative positions of the solenoid coil 103 and the magnetic core 101 according to the present embodiment are adjusted. FIG. 5A illustrates the overall configuration of the actuator 30 and the coil unit 10 coupled to each other. FIG. 5B illustrates the configuration in which the solenoid coil 103 has moved forwards and the magnetic core 101 has moved backwards. FIG. 5C illustrates the configuration in which the solenoid coil 103 has moved backwards and the magnetic core 101 has moved forwards.

Referring to FIG. 5A, the distance between the coil 10 and the medical device can be adjusted suitably. There is an advantage of excellent power efficiency when generating magnetic field for controlling the medical device actuated using electromagnetic force. Referring to FIGS. 5B and 5C, the relative positions of the magnetic core 101 and the solenoid coil 103 are adjusted to accelerate the rate of changes in magnetic field applied to the medical device.

The magnetic core 101 focuses magnetic flux generated by the solenoid coil 103, thereby generating a relatively-strong magnetic field. In this case, however, it is difficult to rapidly change the magnetic flux, since the magnetic core 101 increases the inductance of the coil unit 10. Thus, when iterative changes in magnetic field are required as in the rotational movement or hammering movement of the medical device, it is necessary to reduce the influence of the magnetic core 101.

Since the actuator 30 can adjust the relative positions of the magnetic core 101 and the solenoid coil 103, when a rapid change in the magnetic field is required, magnetic flux focusing in the solenoid coil 103 can be efficiently changed by minimizing the influence of the magnetic core 101.

Although the exemplary embodiments of the present invention have been described for illustrative purposes, a person skilled in the art will appreciate that various modifications, additions and substitutions are possible, without departing from the scope and spirit of the present invention as disclosed in the accompanying claims. It should be understood that the scope of the present invention shall be defined by the appended Claims and all of their equivalents fall within the scope of the present invention.

What is claimed is:

1. An electromagnetic actuating device comprising:
   a coil unit generating magnetic field toward a medical device inserted into a human body and including
      a solenoid coil generating the magnetic field in an axial direction,
      a core housing having a fastening hole formed in an inner portion thereof, and
      a magnetic core disposed inside the core housing and focusing magnetic flux generated by the solenoid coil; and
   an actuator driving the coil unit to move back and forth, thereby adjusting rate of change in the magnetic force or magnetic field applied to the medical device, the actuator including
      an actuating screw, and
      a first motor rotating the actuating screw,
   wherein the actuating screw of the actuator is coupled with the fastening hole of the core housing, and
   the magnetic core is configured to move along with the core housing as the driving screw rotates.

2. The electromagnetic actuating device according to claim 1, wherein the coil unit further comprises:
   a coil housing with the solenoid coil wound on an outer circumferential surface of the coil housing, and
   wherein the core housing further comprises one or more splines on an outer circumferential surface of the core housing, the splines guiding the core housing in a straight direction when the actuating screw rotates, and
   the coil housing further comprises one or more spline grooves on an inner surface of the coil housing such that the spline grooves are engaged with the splines, thereby allowing the core housing to slide along the splines grooves.

3. The electromagnetic actuating device according to claim 2, wherein the actuator further comprises:
   a pinion gear; and
   a second motor supplying power to the pinion gear,
   the coil housing further comprises:
   a rack engaged with the pinion gear, and
   wherein the coil housing is configured to move back and forth in line as the pinion gear rotates.

\* \* \* \* \*